United States Patent
Pechstein

(10) Patent No.: US 8,668,822 B2
(45) Date of Patent: Mar. 11, 2014

(54) METHOD FOR OPERATING AN ISFET SENSOR

(75) Inventor: Torsten Pechstein, Radebeul (DE)

(73) Assignee: Endress + Hauser Conducta Gesellschaft für Mess- und Regeltechnik mbH + Co. KG, Gerlingen (DE)

(*) Notice: Subject to any disclaimer, the term of this patent is extended or adjusted under 35 U.S.C. 154(b) by 270 days.

(21) Appl. No.: 12/971,050

(22) Filed: Dec. 17, 2010

(65) Prior Publication Data

US 2011/0147232 A1    Jun. 23, 2011

Related U.S. Application Data

(60) Provisional application No. 61/282,154, filed on Dec. 23, 2009.

(30) Foreign Application Priority Data

Dec. 23, 2009 (DE) .......................... 10 2009 055 297

(51) Int. Cl.
*G01N 27/414* (2006.01)
*G01N 27/333* (2006.01)

(52) U.S. Cl.
USPC ........... 205/789; 204/406; 204/422; 204/433; 205/787.5; 257/253

(58) Field of Classification Search
USPC .......... 204/400, 406, 421, 422, 433; 205/775, 205/787.5, 789; 257/253
See application file for complete search history.

(56) References Cited

U.S. PATENT DOCUMENTS

| | | | | |
|---|---|---|---|---|
| 4,567,006 A | * | 1/1986 | Covington et al. | 264/459 |
| 5,182,005 A | * | 1/1993 | Schwiegk et al. | 204/435 |
| 5,911,873 A | * | 6/1999 | McCarron et al. | 205/789 |
| 2005/0104650 A1 | * | 5/2005 | Feldtkeller | 327/427 |

FOREIGN PATENT DOCUMENTS

| | | |
|---|---|---|
| DE | 37 34 634 A1 | 5/1989 |
| DE | 198 57 953 A1 | 7/2000 |
| EP | 1 484 605 A2 | 12/2004 |
| EP | 1 927 852 A1 | 6/2008 |

* cited by examiner

*Primary Examiner* — Susan D Leong
(74) *Attorney, Agent, or Firm* — Bacon & Thomas, PLLC

(57) ABSTRACT

A method for operating an ion-sensitive sensor with a measurement circuit which includes an ion-sensitive electrolyte-insulator-semiconductor structure (EIS); wherein the measurement circuit is embodied to issue an output signal which is dependent on ion concentration, especially a pH value, of a measured liquid; and wherein the method comprises the steps of: introducing the ion-sensitive electrolyte-insulator-semiconductor structure into a measured liquid; accelerating charging processes in the region of an insulator layer of the ion-sensitive electrolyte-insulator-semiconductor structure by operating the sensor over a predetermined time span at least a first working point; and dynamically adapting the working point to set a second working point, and registering and processing the output signal of the measurement circuit at the second working point.

20 Claims, 2 Drawing Sheets

METHOD FOR OPERATING AN ISFET SENSOR

CROSS-REFERENCE TO RELATED APPLICATION:

This application is a Nonprovisional which claims the benefit of U.S. Provisional Application Ser. No. 61/282,154 filed on Dec. 23, 2009.

TECHNICAL FIELD

The invention relates to a method for operating an ion-sensitive sensor, wherein the sensor has a measurement circuit, which includes an ion-sensitive electrolyte-insulator-semiconductor structure (EIS structure), wherein the measurement circuit is embodied to issue an output signal, which is dependent on the ion concentration (especially pH value) of a measured liquid. The invention relates furthermore to an ion-sensitive sensor for determining an ion concentration (especially a pH value) in a measured liquid, wherein the ion-sensitive sensor has a measurement circuit, which includes an EIS structure, and which is embodied to issue an output signal, which is dependent on the ion concentration of the measured liquid.

BACKGROUND DISCUSSION

A sensor with an electrolyte-insulator-semiconductor structure (abbreviated EIS structure), comprises a semiconductor substrate on which an insulator is arranged, which, during measurement mode is supplied with an electrolyte. Ion-sensitive field effect transistors (ISFETs) are established examples of sensors with an EIS structure, wherein, in this case, the insulator forms the ion-sensitive gate insulator of a field effect transistor.

In the case of the so-called LAPS (short for Light-Addressable Potentiometric Sensors), by means of a modulated light signal, photoelectrons are produced in the semiconductor material of an EIS structure, wherein the generation of photoelectrons, again, depends on the electrolyte properties. A basic description of LAPS is given by Hafeman et al. in "Light addressable potentiometric sensor for biochemical systems", Science 240 (1988) 1182-1185.

ISFETs are more established and better investigated than other EIS structures. Therefore, in the following description of problems in the state of the art, reference is essentially made to ISFETs, wherein it is inherent that the described problems and the solution of the invention with all described embodiments are correspondingly given for other sensors with an EIS structure.

An ISFET is an ion-sensitive field effect transistor with a semiconductor substrate, a source, a gate and a drain, which, depending on the particular embodiment of (and especially choice of material for) its gate, can, based on the conductivity of the transistor, measure an ion concentration in a measured liquid (e.g. a concentration of $H^+$, or $H_3O^+$ ions) and therewith the pH value of the measured liquid.

Sensors with ion-sensitive field effect transistors (in the following abbreviated to ISFET sensors) are used for measuring ion concentrations or special substance concentrations in liquid measured media of different compositions and conductivities. Application of ISFETs for continuous detection of concentrations occurs in environmental monitoring, in industrial process monitoring, in the foods industry and in biochemistry/medical technology. ISFET sensors are especially wide spread for determining the concentration of $H^+$, or $H_3O^+$ ions and the pH value derived therefrom in a measured liquid. Important in the case of the applications of the ISFET sensors named above is a highly precise concentration registration and a fast start-up, while at the same time maintaining an acceptable price.

The ion concentration (or the pH value) to be determined for a measured liquid at the gate of the ISFET influences the channel resistance of the ISFET, which, for example, in the case of applying a constant voltage between the source and drain, expresses itself in a change in the channel current. Exploiting this effect, the measurement circuit of an ISFET sensor produces an output signal, which is correlated with the ion concentration or the pH value of the measured liquid. Different measuring electronics for a pH ISFET sensor are known, for example, from "Analytical and Biomedical Applications of Ion Selective Field-Effect Transistors" P. Bergveld, A. Sibbald, Elsevier Science Publishers B.V., Amsterdam 1988, Chapter 8, ISFET Instrumentation, Pgs. 101-107.

The measurement circuit can, for example, be embodied in such a manner, that the channel current between the drain and source is held constant. This can, for example, be achieved by application of a negative feedback circuit, which impresses upon the reference electrode (or, alternatively, the source-electrode) a potential required for holding the channel current constant.

The gate of an $H^+$, or pH, sensitive ISFET includes an $H^+$, or pH, sensitive layer (for example of $Al_2O_3$, $Si_3N_4$ or $Ta_2O_5$), which, for measuring, is brought directly in contact with the measured liquid. For ISFET sensors having a $Ta_2O_5$ gate layer, upon turning on the measuring electronics, it can especially be observed that the output signal of the sensor first reaches a stable value after some minutes. Only after reaching a stable value, however, is the performing of measurements possible with sufficient accuracy.

SUMMARY OF THE INVENTION

An object of the invention is to provide a method for operating a sensor—and to provide a sensor of the previously named type—wherein the time span, which lies between turning the sensor on and the point in time when a sufficient accuracy of measurement for the sensor is assured, is lessened.

This object is achieved by a method for operating an ion-sensitive sensor with a measurement circuit, wherein the circuit includes an ion-sensitive electrolyte-insulator-semiconductor structure (EIS); wherein the measurement circuit is embodied to issue an output signal, which is dependent on ion concentration of a measured liquid; and comprising the steps of:
 introducing the ion-sensitive electrolyte-insulator-semiconductor structure into a measured liquid;
 accelerating charging processes in the region of an insulator layer of the ion-sensitive electrolyte-insulator-semiconductor structure (especially at the interface between the ion-sensitive insulator layer of the electrolyte-insulator-semiconductor structure and the measured liquid) by operating the sensor over a predetermined time span at least a first working point; and
 dynamically adapting the working point to set a second working point and registering and processing the output signal of the measurement circuit at the second working point.

This method is based the idea that the previously described behavior upon turning-on is influenced by the surface structure of the ion-sensitive layer. The surface of these layers (especially of crystalline $Ta_2O_5$ layers) is not perfectly planar, since they are composed of mutually adjoining crystallites of different sizes. The thus resulting roughness of the surface lies in the range of 1 to 10 nm. Due to this surface structure, in addition to almost planar regions, vertical surfaces, which are exposed to the measured liquid, are also present.

The switching in of an external electrical field through the introduction of the ion-sensitive EIS structure into the measured medium and the turning on of the measurement circuit effects a polarization of the ion-sensitive layer, which leads to a change in the space charge zone at the interface between the ion-sensitive layer and the measured solution. This results, in turn, in a new alignment of the short-range ordering of the ions, e.g. of $H_3O^+$ ions and $OH^-$ ions, present at the interface of the measured liquid. In the case of applying an external electrical field, different field conditions are present in the planar regions and in the vertical surfaces. This leads to the fact that the formation of an equilibrium state at the interface occurs very slowly, i.e. over a time period of some minutes.

Through dynamic changing of the working point of the sensor between a first working point (which is provided at start-up of the sensor for acceleration of the charging processes at the interface) and a second working point (which is provided for the actual measurement mode), the start-up time period (i.e. the period of time needed to reach a state of equilibrium at the interface) can be significantly shortened.

The ion-sensitive layer of the EIS structure is insulated from the semiconductor substrate of the EIS structure, so that a capacitor is present. When a voltage $U_1$ is applied across the capacitor, the capacitor is charged with a charge $Q_1$, which is related to the voltage U according to the formula for capacitance C of the capacitor as follows:

$$C = \frac{Q_1}{U_1}.$$

The charging by electrical current flow i is a function of time according to the formula:

$$Q_1 = \int i \, dt.$$

If the voltage $U_1$ is increased to a voltage $U_2$, the capacitor is charged with an increased charge $Q_2$. More charge is then transported per unit time.

Thus, if, when turning on the sensor, a voltage $U_2$ (which is increased with respect to the voltage $U_1$, which is present across the ion-sensitive layer during the measurement mode) is applied across the ion-sensitive layer, and this voltage sinks to the level of $U_1$ at a point in time when the capacitor is charged with the charge $Q_1$, the charging process on the ion-sensitive layer requires considerably less time than in the case of a conventional start-up, in the case of which the voltage present across the ion-sensitive layer is not changed.

The time span within which the sensor is operated at the first working point, can lie, for example, between 5 s and 60 s.

In a method variant, the ion-sensitive electrolyte-insulator-semiconductor structure is part of an ion-sensitive field effect transistor with a semiconductor substrate, an ion-sensitive gate, a source and a drain; wherein the measurement circuit includes a reference half-cell, which, together with the ion-sensitive gate, is exposed to the measured liquid.

In a further development of this method variant, a bias voltage is effected between the substrate and the reference electrode by feeding to a first input of an operational amplifier (whose output is connected with the reference half-cell) via a voltage divider formed from the ion-sensitive field effect transistor and an additional resistor, an operating voltage of the measurement circuit, and by feeding a reference voltage to a second input of the operational amplifier.

Especially for dynamic adapting of the working point of the ion-sensitive field effect transistor for the acceleration of the charging processes at the gate during start-up (or when turning the device on), the voltage divider can, in such case, be supplied with an activating voltage, which is formed from a sum of the operating voltage and an additional voltage, so that the sum of the operating voltage and the additional voltage is fed to the first input of the operational amplifier.

For forming the activating voltage, another voltage source which delivers an additional voltage can be connected in series with the voltage source which delivers the operating voltage.

The object is furthermore achieved by an ion-sensitive sensor for determining an ion concentration, especially a pH value, in a measured liquid, wherein the ion-sensitive sensor has a measurement circuit, which includes an ion-sensitive electrolyte-insulator-semiconductor structure, especially an ion-sensitive field effect transistor, and which is embodied to issue an output signal, which is dependent on ion concentration of the measured liquid;

wherein the ion-sensitive sensor can be operated in a measuring mode at a predetermined working point;

and wherein the working point of the ion-sensitive sensor is dynamically adaptable, in order to accelerate charging processes in the region of an insulator layer of the ion-sensitive electrolyte-insulator-semiconductor structure, especially at the interface between the insulator layer and the measured liquid.

The sensor can, thus, in addition to the measuring mode, be operated in a further mode—a charging mode or activating mode—wherein, in the measuring mode and in the charging mode, the sensor can be operated at different working points. Present at the different working points are different voltages, especially across the capacitor formed by the ion-sensitive layer and the substrate.

In an embodiment, the measurement circuit includes an ion-sensitive field effect transistor with a substrate, a source, a drain and an ion-sensitive gate, as well as a reference half-cell, wherein the ion-sensitive gate and the reference half-cell are contactable with the measured liquid. There arises in this manner an electrical contact between the gate and the reference half-cell via the measured liquid, which acts as an electrolyte. In this embodiment, charging processes at the gate can be accelerated by dynamically adapting the working point of the sensor.

In a further development of this embodiment, the measurement circuit has an operational amplifier with a first input, to which is connected a tap of a voltage divider formed from the ion-sensitive field effect transistor and an additional resistor, wherein the operational amplifier has a second input, to which a reference voltage is applied, and an output, which is connected with the reference half-cell, wherein, in the measuring mode, an operating voltage is applied to the voltage divider.

For dynamically adapting the working point, the measurement circuit can include at least one other voltage source, which can be connected in series with the operating voltage and the voltage divider.

The output signal of the measurement circuit corresponds to the output signal of the operational amplifier, which serves to impress upon the reference half-cell an opposing voltage of equal size and opposite sign to the electrical effect of a pH change at the gate of the ISFET, so that, during the measurement mode, the gate remains in charge equilibrium. The output signal of the operational amplifier is thus correlated with the measured value to be determined (i.e. the ion concentration to be determined or the pH value to be determined), and can, consequently, serve as a measurement signal.

The sensor is, for example, a sensor for determining the pH value of a measured liquid, wherein the ion-sensitive gate comprises a $Ta_2O_5$ layer, which, in the measurement mode, comes directly in contact with the measured liquid.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
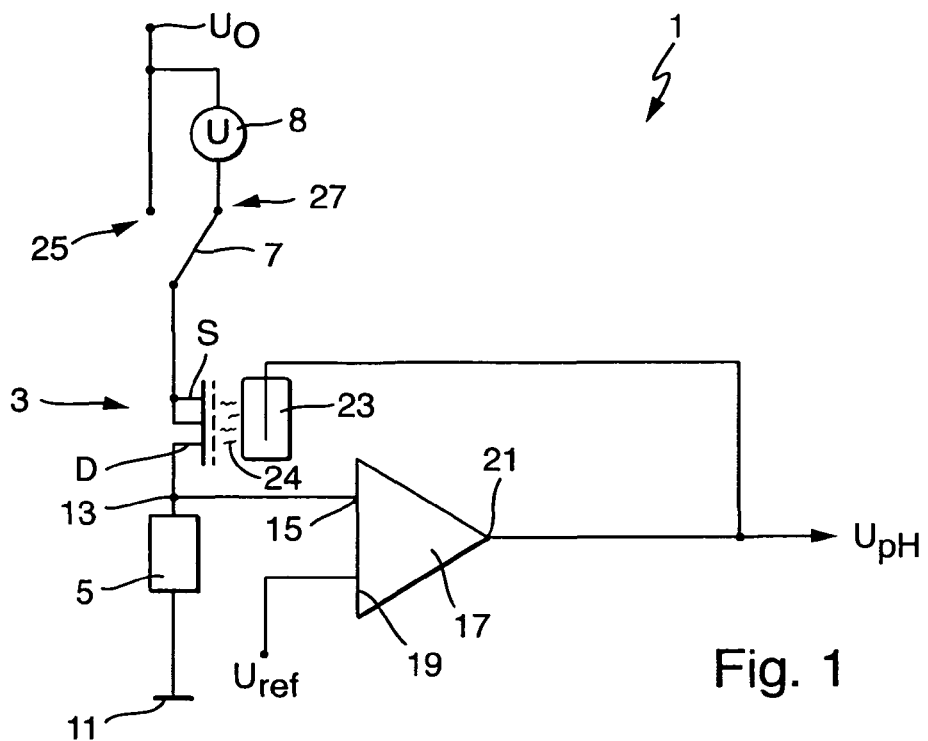
FIG. 1 a measurement circuit with an ISFET sensor.

FIG. 1 shows an example of measuring electronics of an ISFET sensor 1 utilizing an ion-sensitive field effect transistor (ISFET) 3. The ISFET 3 has a gate comprising a pH value sensitive $Ta_2O_5$ layer, as well as a source S and a drain D. The ISFET 3 is a component of a voltage divider, which includes the resistance of the ISFET 3 and an additional resistor 5, which is connected in series with the ISFET 3. Applied across the voltage divider, depending on the position of the switch 7, is either the operating voltage $U_o$ or a sum of the operating voltage $U_o$ and the voltage U delivered by an additional voltage source 8. The operating voltage $U_o$ is, in the present example, present between a feeding location 9 and a ground 11, between which are connected the resistance of the ISFET 3 and the resistor 5, which are connected in series. The tap 13 of the voltage divider is connected with the first input 15 of the operational amplifier 17. Present at the second input of 19 of the operational amplifier 17 is a reference voltage $U_{ref}$. The output 21 of the operational amplifier 17 is connected with a reference half-cell 23. The reference half-cell 23 is, in the measurement mode, in electrical contact with the ion-sensitive gate of the ISFET via a measured liquid 24. The measured liquid 24 can be, for example, an aqueous solution, which contains a concentration of particular ions (especially $H^+$ or $H_3O^+$ ions or the pH value derived therefrom) to be ascertained. In the present example, the measured liquid 24 is a water sample, whose pH value is to be ascertained by the ISFET sensor 1.

The operational amplifier 17 serves as a control element, which, on the basis of the change of the potential applied to the first input 15, impresses on the reference half-cell 23 an opposing voltage of equal size and opposite sign counteracting the electrical effect of the pH change at the gate of the ISFET 3. The output signal $U_{pH}$ of the operational amplifier 17 is a measure for the pH value present in the measured liquid 24, and, as a measurement signal, is output to evaluation and display electronics (not shown), for example, a measurement transmitter.

In the measurement mode, the ISFET sensor 1 closes the contact 25 of the switch 7, so that $U_o$ is present at the voltage divider.

For accelerating charging processes at the gate which occur during start-up, i.e. when turning the ISFET sensor on, i.e in the case of switching in the voltage $U_o$ after immersion of the gate into the measured liquid 24, the additional voltage source 8 can be switched in by actuating the switch for closing the contact 27. Then present at the voltage divider is the sum $U_o+U$ of the operating voltage $U_o$ and the voltage U which the additional voltage source 8 delivers.

Figure 2:
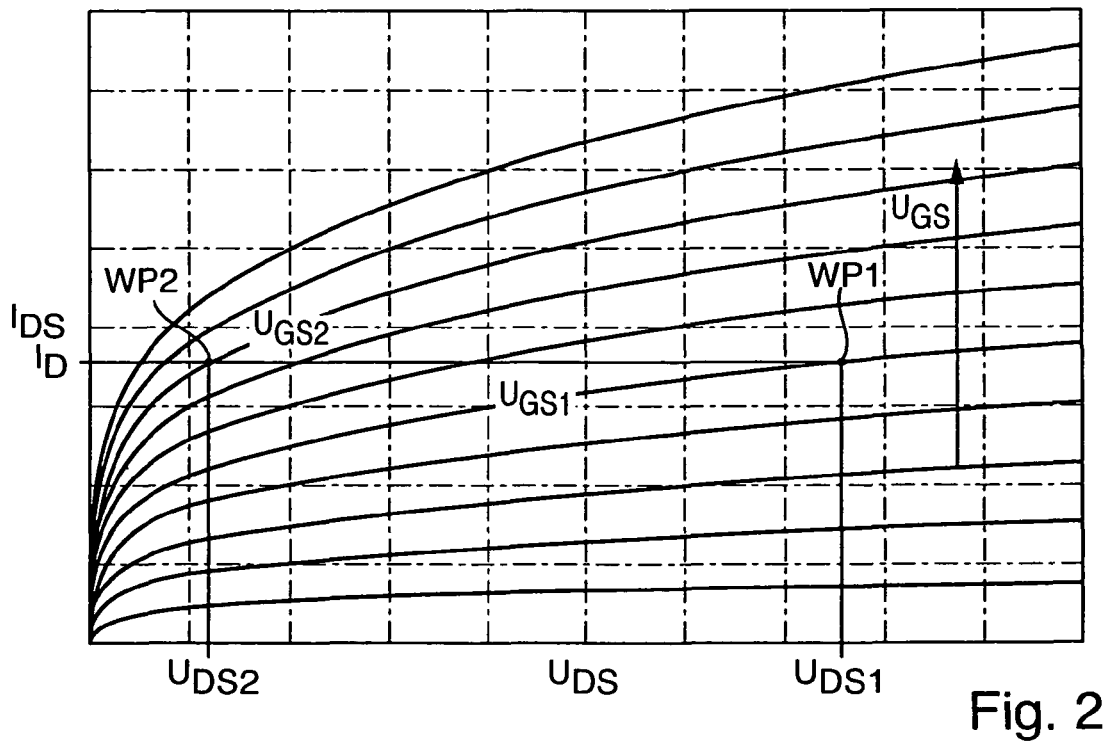
FIG. 2 a set of characteristic curves of IDS versus UDS of an ISFET.

FIG. 2 shows a set of characteristic curves of $I_{DS}$ versus $U_{DS}$ of an ISFET. $I_{DS}$ refers to the drain-source electrical current which flows between the drain and source, and $U_{DS}$ refers to the voltage which is present between the drain and source. Each characteristic curve of the chart illustrated in FIG. 2 gives the drain-source electrical current $I_{DS}$ as a function of the drain-source voltage $U_{DS}$ in the case of a predetermined, fixed, gate-source voltage $U_{GS}$ between the gate and source, and, therewith, also between the gate and substrate of the ISFET. The higher the gate-source voltage $U_{GS}$, the stronger is the rise in the drain-source-electrical current $I_{DS}$ with the drain-source-voltage $U_{DS}$.

FIG. 2 shows the dynamic working point adapting for a measurement circuit with an ISFET in constant electrical current mode: For the measurement mode, in the case of which a pH value-dependent output signal issued by the measurement circuit is registered and processed as a measured value, a first working point WP1 at a first drain-source-voltage $U_{DS1}$ and an associated drain-source-electrical current $I_{DS1}$ can be selected. The working point WP1 lies on a first $I_{DS}/U_{DS}$ characteristic curve in the case of a gate-source voltage $U_{GS1}$.

If the drain-source voltage $U_{DS1}$ is connected to an ISFET which is immersed in a measured liquid, this also being referred to as turning on the ISFET sensor, then the charging processes at the gate, as described above, first take place. In the case of a drain-source-voltage $U_{DS1}$ as usually selected for ISFET sensors, these processes can require some minutes. In order to accelerate these processes, the working point of the ISFET sensor can be dynamically adapted, by applying a second drain-source-voltage $U_{DS2}$, which is different from that in the measuring mode. In the constant electrical current mode of the example considered here, this corresponds to a shifting of the working point to the point WP2. Since $I_{DS}$ remains constant here, this corresponds to a changing of the characteristic curve, or an increasing of the gate-source voltage $U_{GS}$. The working point WP2 thus lies on a second $I_{DS}$ versus $U_{DS}$, characteristic curve at an increased gate-source voltage $U_{GS2}$.

Such a adapting of the working point is possible with the measurement circuit illustrated in FIG. 1 by actuating the switch 7 for switching the additional voltage source 8 in and out.

The gate of the ISFET is insulated from the substrate, also referred to as bulk; a capacitor with the capacitance $C_{GB}$ is thus present between the gate and substrate. When the gate-source voltage $U_{GS1}$ is applied, the capacitor is charged with the charge $Q_{GS1}$. $U_{GS1}$ is proportionally related to the charge $Q_{GS1}$ via a constant $C_{GS}$, as is described above. When the gate-source voltage $U_{GS1}$ is increased to a higher gate-source voltage $U_{GS2}$, since the charging is a time-based process according to $$Q_{GS}=\int I_{DS}dt$$

more charge per unit time is transported. In the case of an increased gate-source voltage $U_{GS2}$, the capacitor is fully charged with a higher charge $Q_{GS2}$. When the increased gate-source voltage $U_{GS2}$ is reduced back to $U_{GS1}$ at a point in time when the capacitor is essentially, or almost, charged with the charge $Q_{GS1}$, a shorter, or even minimal, time span for the charging processes at the gate can be achieved—i.e., a shorter turning-on time for the ISFET sensor, before the elapse of which the ISFET sensor delivers no reliable measured values.

Figure 3:
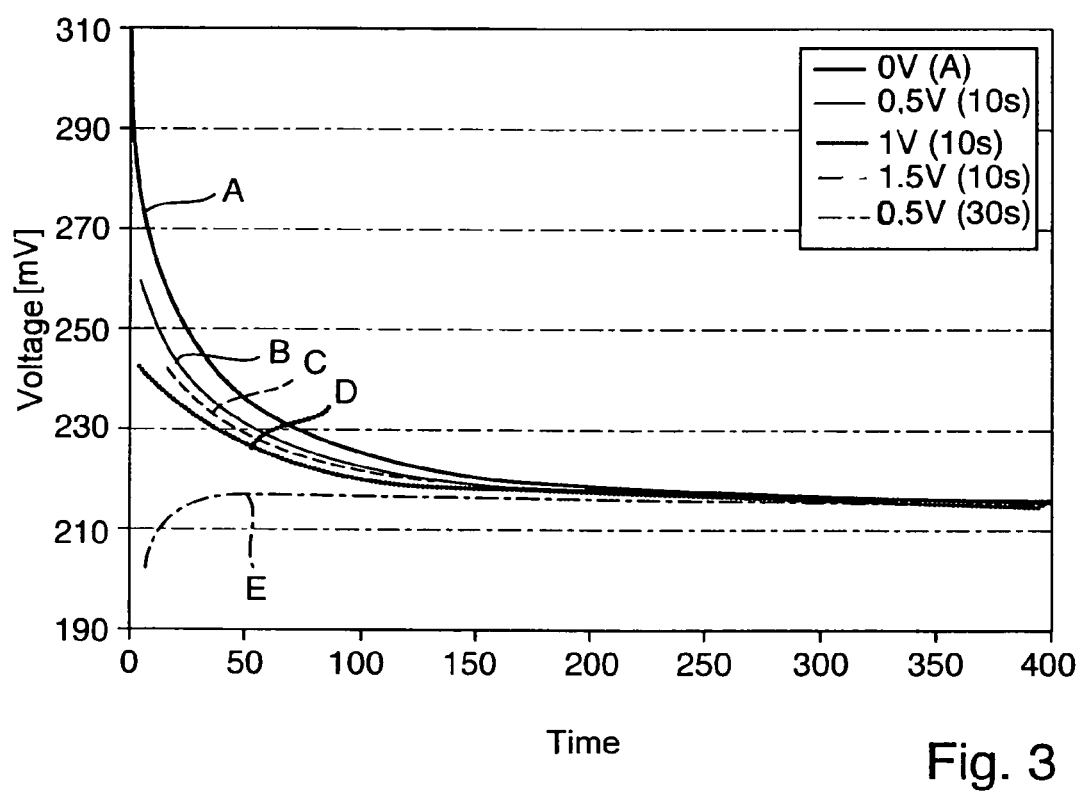
FIG. 3 a graph showing ISFET sensor signal as a function of the time after turning on the measuring circuits illustrated in FIG. 1 in the case of different voltages U.

FIG. 3 shows a graph, in which the output signal $U_{pH}$ of the operational amplifier 17 serving as the measurement signal of the ISFET sensor 1 is presented as a function of time. Curve A shows the typical curve of the measurement signal $U_{pH}$ after the ISFET sensor 1 is turned on, i.e. after switching in the operating voltage $U_o$, in the case of a position of the switch 7, in which the contact 25 is closed. As can be gathered from the diagram, only after, for instance, 300 s to 400 s does the measurement signal $U_{pH}$ asymptotically approach the limit value of the measurement signal corresponding to the measured value to be ascertained. The additional curves B to E illustrated in FIG. 3 correspond to the curve of the measurement signal $U_{pH}$ after—in addition to the operating voltage $U_o$—the other voltage source 8 was (by actuating the switch 8 to close the contact 27) initially switched in for a predetermined time span. In such case, both the length of the predetermined time span, as well as the magnitude of the additional voltage U delivered by the voltage source 8, was varied. After the particular predetermined time span had elapsed, the switch 7 was moved to close the contact 25, so that only $U_o$ still remained on the voltage divider of the circuit in FIG. 1, and the output signal $U_{pH}$ of the operational amplifier 17 was registered as a function of the time, and thus the curves B-E illustrated in FIG. 3 were recorded.

In the case of each the curves B to E, it can be seen that, by the temporary switching in of the additional voltage source 8 and the thereby achieved temporary dynamic adapting of the working point of the ISFET sensor before the switch-over into the measuring mode, a significant shortening of the period of time within which the measurement signal $U_{pH}$ reaches a stable limit value (i.e. until the sensor delivers reliable measured values) is effected. In the present example, the lowest achieved setting time of the sensor was reached by switching in the additional voltage source 8 with a voltage of magnitude of 0.5 V for a time span of 30 s at turning-on of the sensor, and, thereafter, the switch 7 was moved to the close the contact 25, following which the measurement curve E was recorded.

In general, it holds in the turning-on phase of the ISFET sensor that the working point of the ISFET is momentarily (e.g. for 30 s) shifted to higher gate-source voltages. In this way, the turning-on period, especially in the case of a $Ta_2O_5$ ISFET, is shortened. In the set of characteristic curves in FIG. 2, this is shown for a circuit in the constant electrical current mode. Such is also possible in the constant voltage mode ($U_{DS}$ remains constant) or in a mixed mode.

The invention claimed is:

1. A method for operating an ion-sensitive sensor with a measurement circuit which includes an ion-sensitive electrolyte-insulator-semiconductor structure (EIS); said ion-sensitive electrolyte-insulator-semiconductor structure is part of an ion-sensitive field effect transistor (ISFET); said measurement circuit is embodied to issue an output signal, which is dependent on ion concentration of a measured liquid, the method comprises the steps of:
   introducing the ion-sensitive electrolyte-insulator-semiconductor structure into the measured liquid;
   accelerating charging processes in the region of an insulator layer of the ion-sensitive electrolyte-insulator-semiconductor structure by operating the sensor over a predetermined time span at at least a first working point, and
   dynamically adapting the first working point to set a second working point, and registering and processing the output signal of the measurement circuit at the second working point.

2. The method as claimed in claim 1, wherein: the time span amounts to between 5 and 60s.

3. The method as claimed in claim 1, wherein: said ion-sensitive field effect transistor (ISFET) includes a semiconductor substrate, an ion-sensitive gate, a source and a drain; and
   said measurement circuit includes a reference half-cell, which is exposed to the measured liquid along with the ion-sensitive gate.

4. The method as claimed in claim 3, wherein:
   a bias voltage is effected between said semiconductor substrate and a reference electrode by feeding to a first input of an operational amplifier, whose output is connected with said reference half-cell via a voltage divider formed from said ion-sensitive field effect transistor and an additional resistor, an operating voltage of said measurement circuit, and by feeding a reference voltage to a second input of said operational amplifier.

5. The method as claimed in claim 4, wherein:
   dynamic adapting of the first working point of said ion-sensitive field effect transistor, the voltage divider is supplied an activating voltage, which is formed from a sum of the operating voltage and an additional voltage, so that said first input of said operational amplifier is fed the sum of the operating voltage and the additional voltage.

6. The method as claimed in claim 5, wherein:
   for forming the activating voltage, a further voltage source which delivers said additional voltage is connected in series with a voltage source which delivers said operating voltage.

7. An ion-sensitive sensor for determining an ion concentration, in a measured liquid, comprising:
   a measurement circuit, which includes an ion-sensitive electrolyte-insulator-semiconductor structure (EIS), having an insulating layer, said ion-sensitive electrolyte-insulator-semiconductor structure is part of an ion-sensitive field effect transistor (ISFET), said ion-sensitive electrolyte-insulator-semiconductor structure configured to issue an output signal which is dependent on ion concentration of the measured liquid, wherein:
   the ion-sensitive sensor is configured to be operated in a measuring mode at a predetermined first working point, and
   the ion-sensitive sensor is configured to be operated during start up at a second working point for a predetermined time span in order to accelerate charging processes in the region of an insulator layer of the ion-sensitive electrolyte-insulator-semiconductor structure.

8. The ion-sensitive sensor as claimed in claim 7, wherein:
   said ion-sensitive field effect transistor includes a substrate, a source, a drain and an ion-sensitive gate, as well as a reference half-cell; and
   said ion-sensitive gate and said reference half-cell are contactable with the measured liquid.

9. The ion-sensitive sensor as claimed in claim 8, wherein:
   said measurement circuit has an operational amplifier with a first input, to which is connected a tap of a voltage divider formed from said ion-sensitive field effect transistor and an additional resistor;
   said operational amplifier has a second input, to which a reference voltage is applied, and an output, which is connected with said reference half-cell; and
   in the measuring mode, an operating voltage is applied to said voltage divider.

10. The ion-sensitive sensor as claimed in claim 9, wherein:
   for dynamic adapting of said first working point, said measurement circuit includes at least one other voltage source, which can be connected in series with the operating voltage and said voltage divider.

11. The ion sensitive sensor as claimed in claim 8, wherein: the ion sensitive field effect transistor comprises a $Ta_2O_5$ gate layer.

12. The method as claimed in claim 3, wherein: said ion sensitive field effect transistor comprises a $Ta_2O_5$ gate layer.

13. A method for operating an ion-sensitive sensor with a measurement circuit which includes an ion-sensitive electrolyte-insulator-semiconductor structure (EIS); said ion-sensitive electrolyte-insulator-semiconductor structure is part of an ion-sensitive field effect transistor (ISFET); wherein the measurement circuit is configured to issue an output signal, which is dependent on ion concentration of a measured liquid, wherein the method comprises the steps of:

introducing the ion-sensitive electrolyte-insulator-semiconductor structure into the measured liquid;

during start-up of the sensor accelerating charging processes in the region of an insulator layer of the ion-sensitive electrolyte-insulator-semiconductor structure by operating the sensor over a predetermined time span at at least a first working point, and dynamically adapting the first working point to set a second working point, and registering and processing the output signal of the measurement circuit at the second working point.

14. The method as claimed in claim 8, said ion-sensitive electrolyte-insulator-semiconductor structure comprising an ion sensitive layer, which is insulated from the semiconductor substrate of the electrolyte-insulator-semiconductor structure thus forming a capacitor, and wherein, when turning on the sensor, a first voltage is applied across the ion-sensitive layer, and this voltage is decreased to the level of a second voltage at a point in time when said capacitor is charged with a first charge.

15. The method as claimed in claim 8, said ion-sensitive electrolyte-insulator-semiconductor structure comprising an ion sensitive layer, wherein said sensor is turned on and, during start-up of said ion-sensitive sensor, a first voltage is applied across the ion-sensitive layer, and after said predetermined time span, a second voltage is applied across the ion sensitive layer in a measurement mode of said ion-sensitive sensor, wherein said first voltage is higher than said second voltage.

16. The method as claimed in claim 7, wherein: said ion-sensitive field effect transistor (ISFET) comprises a semiconductor substrate, an ion-sensitive gate, a source and a drain; and wherein the measurement circuit includes a reference half-cell, which is exposed to the measured liquid along with the ion-sensitive gate.

17. The method as claimed in claim 8, wherein:

during said measurement mode of said ion-sensitive sensor a bias voltage is effected between the substrate and the reference half cell by feeding to a first input of an operation amplifier whose output is connected with the reference half-cell via a voltage divider formed from the ion-sensitive field effect transistor and an additional resistor an operating voltage of the measurement circuit, and by feeding a reference voltage to a second input of the operational amplifier.

18. The method as claimed in claim 15, wherein: for applying said first voltage across said ion-sensitive layer during start up, a voltage divider is supplied an activating voltage, which is formed from a sum of an operating voltage and an additional voltage, so that a first input of an operational amplifier is fed the sum of the operating voltage and the additional voltage.

19. The method as claimed in claim 18, wherein:

for forming the activating voltage, a voltage source which delivers the additional voltage is connected in series with the voltage source which delivers the operating voltage.

20. An ion-sensitive sensor as claimed in claim 7, said ion-sensitive electrolyte-insulator-semiconductor structure comprising an ion sensitive layer, wherein:

said sensor is adapted to apply a first voltage across the ion-sensitive layer during start-up of said ion-sensitive sensor for said predetermined time span;

to apply a second voltage across the ion sensitive layer in a measurement mode of said ion-sensitive sensor; and said first voltage is higher than said second voltage.

\* \* \* \* \*